United States Patent
Boyette et al.

(10) Patent No.: US 8,158,405 B2
(45) Date of Patent: Apr. 17, 2012

(54) PROCESS FOR CONCENTRATING AND PROCESSING FLUID SAMPLES

(75) Inventors: Scott Boyette, New Hope, PA (US); Rong Xu, Shanghai (CN); Jing Luo, Shanghai (CN); Weiqing Xu, Shanghai (CN); Jing Chen, Shanghai (CN); Weimin Xiao, Shanghai (CN); Tong Chen, Shanghai (CN)

(73) Assignee: General Electric Company, Schenectady, NY (US)

( * ) Notice: Subject to any disclaimer, the term of this patent is extended or adjusted under 35 U.S.C. 154(b) by 798 days.

(21) Appl. No.: 12/215,768

(22) Filed: Jun. 30, 2008

(65) Prior Publication Data

US 2009/0326211 A1 Dec. 31, 2009

(51) Int. Cl.
C12N 1/06 (2006.01)

(52) U.S. Cl. ......... 435/259; 435/6.1; 435/7.2; 435/7.32; 435/7.31; 435/325; 536/25.4

(58) Field of Classification Search .................. 324/259, 324/6.1, 7.2, 7.31, 7.32, 325; 536/25.4
See application file for complete search history.

(56) References Cited

U.S. PATENT DOCUMENTS

| | | | |
|---|---|---|---|
| 4,080,294 A | 3/1978 | Edwards et al. | |
| 4,137,169 A | 1/1979 | El-Hindi | |
| 4,358,535 A | 11/1982 | Falkow et al. | |
| 4,518,402 A | 5/1985 | Dargel | |
| 4,976,876 A | 12/1990 | Diman et al. | |
| 5,096,474 A | 3/1992 | Miller, Jr. et al. | |
| 5,155,018 A | 10/1992 | Gillespie et al. | |
| 5,376,527 A | 12/1994 | Robson et al. | |
| 5,456,835 A | 10/1995 | Castino et al. | |
| 5,458,782 A | 10/1995 | Hou et al. | |
| 5,620,790 A | 4/1997 | Holzki et al. | |
| 5,643,425 A * | 7/1997 | Amano et al. | 204/279 |
| 5,658,714 A | 8/1997 | Westfall et al. | |
| 5,669,946 A | 9/1997 | Blair, Jr. | |
| 5,783,686 A | 7/1998 | Gonzalez | |
| 5,808,041 A | 9/1998 | Padhye et al. | |
| 5,972,613 A | 10/1999 | Somack et al. | |
| 6,015,493 A | 1/2000 | Smith et al. | |
| 6,110,662 A * | 8/2000 | Foung et al. | 435/5 |
| 6,136,555 A * | 10/2000 | Jones | 435/41 |
| 6,312,588 B1 | 11/2001 | Conrad et al. | |
| 6,383,818 B1 | 5/2002 | Arai et al. | |
| 6,405,875 B1 | 6/2002 | Cutler | |
| 6,479,273 B1 | 11/2002 | Bogedain et al. | |
| 6,508,936 B1 | 1/2003 | Hassan | |
| 6,544,424 B1 | 4/2003 | Shevitz | |
| 6,544,751 B1 | 4/2003 | Brandwein et al. | |
| 6,551,642 B2 | 4/2003 | Trout | |
| 6,821,757 B2 | 11/2004 | Sauer et al. | |
| 6,838,272 B2 | 1/2005 | Bogedain et al. | |
| 6,939,697 B2 | 9/2005 | Champluvier et al. | |
| 6,958,392 B2 | 10/2005 | Fomovskaia et al. | |
| 7,220,549 B2 | 5/2007 | Buzby | |
| 7,252,801 B2 | 8/2007 | Coffey | |
| 7,378,238 B2 | 5/2008 | Hilbrig et al. | |
| 7,385,040 B2 | 6/2008 | Johansson et al. | |
| 2003/0201229 A1 | 10/2003 | Siwak et al. | |
| 2004/0033484 A1 * | 2/2004 | Krenn et al. | 435/4 |
| 2005/0115903 A1 | 6/2005 | Hallier-Soulier et al. | |
| 2006/0263773 A1 | 11/2006 | Tanaka | |
| 2007/0003997 A1 * | 1/2007 | Kemmochi et al. | 435/34 |
| 2007/0098674 A1 * | 5/2007 | Bukshpan et al. | 424/78.1 |
| 2007/0185033 A1 * | 8/2007 | Gefter et al. | 514/15 |
| 2007/0202770 A1 * | 8/2007 | Penalva | 442/337 |
| 2008/0013092 A1 * | 1/2008 | Maltezos et al. | 356/417 |
| 2009/0221013 A1 | 9/2009 | Lepeuple et al. | |

FOREIGN PATENT DOCUMENTS

| | | |
|---|---|---|
| EP | 0 958 037 B1 | 8/2003 |
| EP | 0 979 237 B1 | 11/2004 |
| EP | 1 710 011 A1 | 10/2006 |
| EP | 0389 063 B2 | 10/2006 |
| EP | 1 624 950 B1 | 7/2007 |
| FR | 2693474 A | 1/1994 |
| JP | 2003289899 A1 * | 10/2003 |
| WO | WO 00/27510 | 5/2000 |
| WO | WO 02/36248 A1 | 5/2002 |
| WO | WO 03/035234 A1 | 5/2003 |
| WO | WO 2005/115595 A1 | 8/2005 |
| WO | 2006129038 A | 12/2006 |
| WO | WO 2007/004263 A1 | 1/2007 |
| WO | WO 2007/065229 A1 | 6/2007 |

OTHER PUBLICATIONS

Definition of surfactant from www.thefreedictionary.com/Soap+and+Detergent downloaded Apr. 24, 2011, 3 pages.*
Derwent abstract for NL 1021933 C6, published Dec. 2, 2007, downlaoded Apr. 24, 2011 from WEST.*
Machine translation for JP 2003289899 (to Inoue et al.) published Oct. 14, 2003; downloaded Apr. 23, 2011 from JPO (13 pages).*
Yaradou Diaraf Farba et. al., Integrated real-time PCR for detection and monitoring of Legionella pneumophila in water systems, Applied and Environmental Microbiology, Mar. 2007, pp. 1452-1456, vol. 73, No. 5.
International Search Report issued in connection with corresponding PCT Application No. PCT/US2009/046755 on Nov. 3, 2009.

(Continued)

Primary Examiner — Susan Hanley
(74) Attorney, Agent, or Firm — Wegman, Hessler & Vanderburg

(57) ABSTRACT

A method of treating a liquid sample having microbiological target species therein to concentrate the species and collect lysate is disclosed. The liquid sample comprises non-target microbiological particles, inorganic particles, and microbiological target species. The liquid is passed through a prefilter medium to allow the target species to pass through as filtrate and retain non-target microbiological products and inorganic particles thereon. The filtrate is contacted with a main filtration medium adapted to retain the target species thereon as retentate. The retentate is lysed to form a lysate containing target material that was enveloped within the microbiological target species. The microbiological species may comprise cell containing or viral material. Target materials comprise intracellular nucleic acids, or in the case of viral sampling, nucleic acids encased within the protein sheath or coating of the virus.

18 Claims, No Drawings

OTHER PUBLICATIONS

MSDS No. 74385—Nonident P40 Substitute, Fluka, Manufacturer: Sigma-Aldrich, Shanghai, China.

Lambert, K.J., "Pretreatment of Cells of 'Klebsiella pneumoniae' with 50% (v/v) Dimethylsulfoxide Yields Purified Deoxyribonucleic Acid of Low Polysaccharide Content", Agric. Biol. Chem., vol. 46, #12, 1982, pp. 3079-3080.

Lytle, C.D., et al., "Virus Passage through Track-Etch Membranes Modified by Salinity and a Nonionic Surfactant", Applied & Environ. Microbiology, vol. 65, #6, Jun. 1999, pp. 2773-2775.

Taylor, M.T., et al., "Lysing Bacterial Spores by Sonication Through a Flexible Interface in a Microfluidic System", Analytical Chemistry, ACS Publications, vol. 73, #3, Feb. 1, 2001, pp. 492-496.

Nishiguchi, M.K., et al., "DNA Isolation Procedures", Methods and Tools in Bioscience and Medicine, 2002, pp. 249-287.

Law, K.A. et al., "Initial investigations into the ultrasonic lysis of microbial cells for the release of adenosine triphosphate", Analytical Biochemistry, vol. 317, 2003, pp. 266-267.

Amari, M. et al., "A Comparison of the Effect of PTFE and UPE Membrane Filters on the Quality of Photoresist Developers", Mykrolis, www.mykrolis.com, 2004, 9 pages.

VanBavel, E., "Effects of Shear Stress on Endothelial Cells: Possible Relevance for Ultrasound Applications", Progress in Biophysics and Molecular Biology, vol. 93, 2007, pp. 374-383.

"Assay", Wikipedia, http://en.www.wikipedia.org/wiki/Assay, Apr. 23, 2008, 3 pages.

"*Legionella*", Wikipedia, http://en.www.wikipedia.org/wiki/Legionella, May 30, 2008, 4 pages.

"RNA", Wikipedia, http://en.www.wikipedia.org/wiki/RNA, Jun. 6, 2008, 6 pages.

\* cited by examiner

PROCESS FOR CONCENTRATING AND PROCESSING FLUID SAMPLES

FIELD OF INVENTION

The invention pertains to a process for concentrating fluid samples to obtain biological nucleic acid target materials for analysis.

BACKGROUND OF THE INVENTION

Detection and control of microorganisms are important in many fields including health care, environmental regulation, bio-warfare, pathogen identification, food and drug testing, and in a variety of industrial systems. In industry, presence of undesirable microorganisms decreases the efficiency of operating equipment and ultimately increases the cost of associated goods or services. Furthermore, since microorganisms multiply rapidly, presence of microbial activity also causes health risks to the public. There is an increasing concern with pathogenic organisms infecting water and process system and creating increased human, animal, and environmental health risk.

In cooling towers, for example, water borne pathogenic microorganisms such as Legionella sp. may be present. If not properly treated with preferred biocides, aerosolized particles containing the microorganisms can create extreme health concerns from inhalation of the aerosolized microorganisms leading to disease such as Pontiac fever or the sometimes fatal Legionnaire's disease caused by Legionella pneumophila. Detection of this microorganism is difficult in the case of open recirculation water systems such as cooling towers because low concentrations represent serious health risk, and large water volumes must be concentrated into smaller sample volumes in order to perform the desired analytical test and obtain accurate and reproducible results.

SUMMARY OF THE INVENTION

The invention pertains to a method of treating a liquid sample having non-target microbiological particles, inorganic particles, and microbiological target species such as cells or viruses therein. The microbiological target species comprise target materials enveloped therein. The sample is passed through a prefilter medium to allow the target species to pass there through as filtrate. Some of the non-target biological particles and inorganic particles are retained on the prefilter medium. The filtrate from the prefiltering step is contacted by a main filtration medium that is adapted to retain the biological target species thereon as retentate along with other non-target microorganisms. The retentate from the main filtration step is lysed to form a lysate containing the target material.

In another aspect, the cell lysate passes through the main filtration medium and is further contacted by a post filtration medium to retain unlysed cells thereon while allowing passage of the target material therethrough as filtrate.

If desired, the main filtration medium may be pretreated with a retention enhancement agent or agents to improve the retainment of the microbiological target species on the main filter medium. In this case, the main filtration medium may be treated with a member or members chosen from the group consisting of surfactants, chelate reagents, salts, and organic solvents. These treatment agents both maintain the integrity of the microbiological target species therein (e.g., cells and viruses) during the main filter capture step and prevent the microbiological target species from irreversibly adhering to the filter material. This assures that a representative sample can be lysed and produce a testing sample that accurately represents the starting material.

DETAILED DESCRIPTION OF EXEMPLARY EMBODIMENTS

In one aspect, the present invention relates to a sample collection and processing method including filtration and lysis steps. In one exemplary embodiment, the method features membranes to filter high volumes of liquid quickly and collect target components in a liquid by a two-step method including a prefiltration step and a main filtration step. The process deploys a post-concentration mechanical or non-mechanical means to release the desired enveloped target material into the solution. The sample solution is then stabilized for downstream analysis. As used herein, microbiological target species may comprise cellular organisms such as bacteria, algae, fungi, prokaryotes, etc. or viruses. As is well known, in cellular material, the target material, nucleic acid such as DNA or RNA, is located inside the cell. In a virus, the nucleic acid is located with a protein coat. "Lysing", as used herein, is then a rupturing of the cells or protein coat to release the desired target nucleic acid material.

The method, for example, may be used to measure microbiological content. Exemplary microorganisms such as bacteria, virus, algae, fungi, and prokaryotes may be measured in accordance with the method. The biological content to be processed in accordance with the methods may be derived from any water or process system such as process water, drinking water, municipal water, cooling water, personal care product manufacturing, in-process pharmaceutical, or food and beverage processes.

In one exemplary embodiment, membranes are employed in a prefiltration system to remove any inorganic particles and large biological particles. The prefiltration membrane or membranes do not retain the target species. This membrane can be any membrane of a variety of a variety of different materials and pore sizes, but preferably one with a controlled pore size that separates at a fixed dimension. Non-limiting examples of prefiltration membrane materials are nylon, stainless steel, cellulose esters, PTFE, glass fibers, polypropylene, polyvinylchloride, hydrophilic acrylic copolymers, polyether sulfones, polycarbonates, and polyesters. Membranes of different pore sizes can be applied depending on the desired end use application. Non-limiting examples of membrane pore size for the prefiltration system are from about 1 μm, to about 100 μm, more preferably from about 1 μm to about 50 μm, but any membrane that can be used as a prefilter using the instant methods should perform a similar function and should have a well-defined pore size, e.g., a mesh structure to assure that the loss of the target materials on the prefilter membrane is minimized.

In another aspect, plural prefiltration membranes can be provided and are arranged in an upstream to downstream flow orientation. The upstream membrane or membranes will have a higher porosity than the downstream membranes.

Although we do not desire to be held to any particular theory of operation or function, it appears that the prefilter serves two purposes. First, it captures larger particles, fungi, algae, and biofilm that, if allowed to transfer to the main membrane, could agglomerate with organics and small particles and inhibit flow. This results in either long filtration times or the inability to filter the total volume required to create a representative sample. Second, the prefilter traps larger life forms like amoeba that are known to harbor

*Legionella*. In one embodiment, the test is for planktonic *Legionella*, and the amoeba would expel very large numbers of *Legionella* if lysed.

In one exemplary embodiment wherein *Legionella pneumophila* is the desired microbiological target species, a pair of nylon prefiltration membranes may be used with the upstream membrane in the pair having a pore size of about 20 μm with the downstream membrane having pores on the order of about 10-11 μm.

The main filtration medium comprises a membrane designed to retain the desired target species. This species may comprise cellular materials or viruses. This membrane can be any member of a different material or pore size. Nonlimiting examples of membranes that may be used as the main filtration medium are nylon, stainless steel, cellulose esters, PTFE, glass fiber, polypropylene, polyvinyl chloride, hydrophilic acrylic copolymer, polyethersulfone, polycarbonate, and polyester. The main filtration membrane functions to retain the target component thereon as retentate. At the same time, in another aspect of the invention, after the microbiological target species containing the target material therein are lysed, the lysate may be capable of passing through the main filtration medium for subsequent downstream assay or other process.

In one aspect of the invention, the lysate may be prevented from passing through the main membrane by placing a barrier on the bottom of the membrane. The lysing action may be performed by shaking, and the lysed product may be extracted through a post concentration membrane (e.g., PES 0.2 μm).

In those instances wherein the lysate is capable of passing through the main membrane, in one embodiment, the lysate could be recirculated in a closed system on multiple passes through the main filter for a predetermined recycling time. Then, the lysate continuing the target material nucleic acid could be removed from the recirculation system for subsequent analysis.

In one embodiment wherein *Legionella pneumophila* is the desired biological target material, glass fiber main filtration members may be used and those having pore sizes of between about 10 μm to about 3.0 μm may be mentioned as exemplary. More preferred are those main filter membranes having pore sizes on the order of between about 0.7 μm to about 2.7 μm.

The main membrane pore size requires consideration of two characteristics. First, it must retain the desired target species thereon while not allowing them to stick to the membrane and be lysed to release the enveloped target material during the concentration step. In that case, the target materials such as nucleic acids would be released during the concentration step and be passed with the filtrate. It is desired to keep the target species (e.g., cellular and viral) intact during the concentration step so that they can be lysed during the lysing step. Second, the membrane should have sufficient porosity to assure that a large volume of sample can be filtered in a time that is practical for efficient sample testing.

The main filter membrane, in accordance with one aspect of the invention, may be treated with chemical or fluidic retention enhancement agents such as surfactants, acids, bases, chelating reagents, salts, organic solvents, etc., to enhance target species retention on the main filtration medium while allowing practical sample flow through the membrane. Suitable surfactants include zwitterionic surfactants, anionic surfactants, cationic surfactants, and nonionic surfactants.

The filtration system including both the prefiltration and main filtration media can, in one embodiment, filter quantitative broad volumes of liquid samples with high flow rates. For example, an exemplary sample volume could be 10 liters or more. The sample could be filtered by an integral filtration system with gravity or pressure assistance. Filtration by pressure includes negative pressure and positive pressure. As is conventional in the art, pumps could be used to make negative pressure such as vacuum air pumps, diaphragm liquid pumps, peristatic pumps, etc.

The target species, such as microbiological contents retained by the main filtration medium, could be used for different applications like physical, chemical, and biological characterization, etc. In processing biological contents, the main membrane containing the desired target cells is exposed to a lysing buffer designed to produce a small volume of stabilized lysate containing nucleic acid and proteins, etc. for downstream detection such as Polymerase Chain Reaction (PCR), real time PCR, reverse transcription realtime PCR, etc. or other molecular test methods. Good integrity of the nucleic acid released from the target species can be obtained if the appropriate lysing material is used and can be stabilized in the lysate for 72 hours or more at temperatures of from about 4° C.-43° C.

Target species lysing occurs by cell or protein envelope rupture and can be classified as including non-mechanical or mechanical methods. Non-mechanical methods include chemical methods, thermal methods, enzymatic methods, etc. Mechanical methods include ultrasonic disruption using a homogenizer; pressing using, for example, a French press, etc., decompression, pulverization, etc.

For non-mechanical methods, a non-limiting example is a chemical lysis method that would include any suitable chemical that can disrupt cell or protein envelope barriers. Detergents are a non-limiting example of chemicals that are commonly used to disrupt a lipid double layer membrane to release cell contents and lyse membrane protein, and non-limiting examples of suitable lysing chemicals are lithium dodecyl sulfate, CHAPS, Tween-20E, NP40, CTAB, PVPP, Triton X series detergents, sodium cholate, and sodium deoxycholate, guanidinium hydrochloride, or caustic. Chaotropic agents like guanidiunium salts can also act as lysing agents in this system. The lysing efficiency of detergents and alternate lysing agents is dependent on the cell types and specific applications. Enzymes such as lysozymes, mutanolysin, labiase, lysostaphin, lyticase, proteinase K, endolysin and achromopeptidases may be included as lysing reagents or additives to enhance lysing. Organic solvents, such as DMSO, DMF could be also included as lysing reagents or additives to enhance lysing. A host of bioscience suppliers offer a wide collection of lysing buffers suitable for cell lysis application. A variety of physical methods such as shaking, heating, cutting and homogenizing, etc., could be employed in the process to enhance the lysing efficiency. Indeed in one embodiment a cutting action may be employed in which the cells may be ruptured and the main membrane itself will be cut. Based on the complexity of the application and the nature of the target species types, single or combinations of chemical lysis methods could be used in combination with mechanical methods.

To remove the interference from undesirable cell lysates and non-lysed cells, an additional membrane or membranes could be added to process the cell lysate for downstream application. The membrane could be any membrane of different materials whose pore size is in the range of 0.22 μm to 0.45 μm for bacterial, yeast, fungi, or protogen sampling. (Virus sampling will require smaller pore sizes). Non-limited examples of these "post" filtrations membrane materials are PVDF, PES, polycarbonate, nylon, etc. This membrane acts primarily to remove large materials and/or unlysed cells from the sample to enhance long term stability of the lysate at the conditions noted above.

Although the current description emphasizes a sample concentration and process method, it is clear that the methods could be applied to laboratory, field applications, on-line, automated batch, or off-line monitoring systems as well. This expansion of capabilities allows the system to be applied to both water and in-process monitoring, as well as final process or product monitoring. Additionally, this method should be readily adapted to process flows that are known to be susceptible to microbiological growth and is not limited to water systems. Processing food, beverage, and personal care products and other systems are within the scope of this invention.

The invention will be further described in the following examples which are to be regarded as being illustrative of the invention and should not be used to limit the claims.

Procedure
1. Spike specific concentration (such as 10^4 CFU) of *Legionella pneumophila* cells and 10^6 CFU of *Pseudomonas fluorescens* into 500 ml of synthetic or field water. For field cooling water, 500 ml raw water without spiking was prepared.
2. Filter 500 ml water sample through Nylon 20 μm (Millipore NY2004700) and Nylon 11 μm (Millipore NY1104700) to remove any particles and large biological contents while not retaining target contents.
3. The filtrate from step 2 was concentrated by surfactant treated glass fiber 2.7 μm (Millipore APFD04700) to retain the target species contents.
4. The main membranes from step 3 were added with 3 ml lysis buffer and lyzed for 5 minutes with the shaking speed of 100 round/minute. The lysis buffer solution comprises lithium lauryl sulfate, DMSO, and ethoxylated nonyl phenol.
5. The lysates were filtered through PES 0.22 μm~0.45 μm membranes for downstream analysis.
6. For each process analysis on synthetic water, the controls are the same amount of target content detection by lysis without concentration.
7. All the downstream analyses are RNA-based methods, except specific DNA-based real time PCR analysis mentioned in the results legends.

EXAMPLES

Example 1

Membrane Screening

A variety of different membrane types were tested as prefilter or filter media so as to ensure that they were capable of filtering a 500 ml cooling water sample within a 10-minute time period. Tested, acceptable materials were found as follows.

| Vendor | Material | Pore Size (μm) |
|---|---|---|
| — | Stainless Steel | 35 |
| Millipore | Polypropylene | 25 |
| Millipore | Polypropylene | 10 |
| Millipore | Nylon | 20 |
| Millipore | PES | 0.22 |
| Millipore | Glass fiber | 1.6 |
| Millipore | Glass fiber | 1.2 |
| Millipore | Glass fiber | 2.7 |

-continued

| Vendor | Material | Pore Size (μm) |
|---|---|---|
| Millipore | Polypropylene | 1.2 |
| Millipore | Polypropylene | 2.5 |
| Millipore | Cellulose ester | 1.2 |
| Millipore | Glass fiber | 0.7 |
| Millipore | Glass Fiber | 0.2-0.6 |
| Millipore | Glass Fiber | 0.8-8.0 |
| Millipore | Glass Fiber | 0.7 |
| Millipore | Nylon | 0.45 |
| Millipore | Nylon | 11 |
| Millipore | Nylon | 11 |
| Millipore | Nylon | 30 |
| Millipore | PES | 0.22 |
| Millipore | Mixed cellulose esters | 0.45 |
| Millipore | Mixed cellulose esters | 8 |
| Millipore | PTFE | 0.45 |
| Millipore | PTFE | 5 |
| Millipore | PTFE | 10 |
| Millipore | Glass fiber | 2.7 |
| Millipore | PES | 0.45 |
| Millipore | PVDF | 0.22 |
| Pall | PP | 10 |
| Pall | Acrylic | 3 |
| Pall | Acrylic | 0.45 |
| Pall | Acrylic | 0.8 |
| Pall | PVC | 5 |
| GE Osmonics | polycarbonate | 0.1 |
| GE Osmonics | polycarbonate | 0.4 |
| GE Osmonics | polycarbonate | 1.0 |
| GE Osmonics | polycarbonate | 0.2 |
| GE Osmonics | polycarbonate | 12.0 |
| GE Osmonics | polycarbonate | 1.0 |
| GE Osmonics | polycarbonate | 2 |
| GE Osmonics | polycarbonate | 3 |
| GE Osmonics | polycarbonate | 5 |
| GE Osmonics | polycarbonate | 10 |
| GE Osmonics | polycarbonate | 20.0 |
| GE Osmonics | polyester | 5 |
| GE Osmonics | polyester | 0.4 |
| GE Osmonics | polyester | 1.0 |
| GE Osmonics | polyester | 10.0 |
| GE Osmonics | polyester | 0.2 |
| GE Osmonics | PES | 0.45 |
| GE Osmonics | PES | 0.4 |
| GE Osmonics | PES | 0.5 |
| GE Osmonics | PES | 0.8 |
| GE Osmonics | PES | 5 |
| GE Osmonics | PES | 10.0 |
| GE Osmonics | PES | 1.2 |
| GE Osmonics | PES | 20.0 |
| GE Osmonics | Nylon | 20.0 |
| GE Osmonics | Cellulose Acetate | 0.45 |
| GE Osmonics | PVDF | 0.22 |
| GE Osmonics | PVDF | 0.45 |
| GE Osmonics | polypropylene | 0.45 |
| GE Osmonics | polypropylene | 0.22 |

Example 2

Prefilter, Main Filter System Test

The performance of a filtration system integrating a combination of Nylon 20 μm and Nylon 11 μm as the prefiltration membranes and a glass fiber 2.7 μm main filtration membrane was assessed to see if it could effectively provide filtration of a 500 ml cooling water sample within 10 minutes. The following results that were obtained indicate the percentage of filtrations passing the criteria versus total test runs. As can be seen in the results, the cooling water tested was taken from Chinese geographic locations and European locations.

The performance of filtration system integrating Nylon 20 μm, Nylon 11 μm as prefiltration membrane and glass fiber 2.7 μm as main membrane.

| | 500 ml field sample flow rate summary (within 5 min) | | | | | |
|---|---|---|---|---|---|---|
| | Filter set | | | | | |
| | Prefiltration | | Main filtration | | Total | |
| Prefilter-prefilter-main filter | China | EU | China | EU | Prefiltration | Main Filtration |
| NY20-NY11-GF2.7 | 94.1% (32/34) | 80% (12/15) | 97.1% (33/34) | 86.7% (13/15) | 89.8% (44/49) | 93.9% (46.49) |

Note:
No specific marked membranes are Millipore brand.
Number in parenthesis shows the number of samples that filtered in less than 10 minutes over the total number of samples.

Example 3

Prefiltration Testing

Candidate pre-filtration membranes were tested to ascertain their efficacy in allowing passage of the target material, *Legionella pneumophila* therethrough. Results are shown in terms of percentage of the desired target retained on the prefilter candidates.

| | |
|---|---|
| Stainless Steel* | 0.64% |
| Nylon 30 μm | 0.31% |
| Millipore NY20 μm | 0.38% |
| Millipore NY11 μm | 1.46% |
| Nylon 20 μm | 22.93% |
| PES 20 μm | 38.52% |
| PC 10 μm | 0.40% |
| PE 10 μm | 0.19% |
| PES 10 μm | 14.62% |
| PC 5 μm | 0.52% |
| PES 5 μm | 15.68% |
| Control | 100% |

*Vendor membranes that are not specifically identified are available from GE Osmonics.

Example 4

Main Membrane Screening for High Cell Retention

Main membrane candidates were screened to ascertain their effectiveness in retaining the desired target material, *Legionella pneumophila* thereon. RNA assay of the target remaining on the main filters was made.

Main membranes screening for high cell retention elucidated by natural log of RNA copies in cells.

| Membrane | Means of RNA Log Copies | STD of RNA Log Copies |
|---|---|---|
| GF2.7 | 7.13 | 0.07 |
| GF1.6 | 7.25 | 0.07 |
| GF1.2 | 7.02 | 0.15 |
| GF0.7 | 7.03 | 0.12 |
| PES0.45 | 7.19 | 0.08 |
| Control | 7.15 | 0.03 |

Example 5

Main membranes were assessed for cell detention after 5 minutes of contact with a lysing buffer system at the prescribed shaking rate noted above. RNA assay of retained cells was made in order to determine the percent yield.

| 500 ml - 5 min Lysis | Yield (%) | STD (%) | RSD (%) |
|---|---|---|---|
| NY20-NY11-GF2.7 | 29.08% | 6.69% | 22.99% |
| NY20-NY11-GF1.6 | 22.32% | 6.17% | 27.66% |
| NY20-NY11-GF1.2 | 30.09% | 8.92% | 29.66% |
| NY11-NY1-GF0.7 | 18.54% | 3.48% | 18.77% |
| NY11-NY1-PES0.45 | 25.60% | 3.41% | 13.33% |

Example 6

Shaking Speed and Lysis Time for Optimized Performance

A series of tests were undertaken to assess lysis solution contact time with the target material and shaking time of the main membrane and retained target. Yield percent was measured by RNA assay of the target material.

DoE Experiments to Determine the Shaking Speed and Lysis Time

| Run | A: Speed (50 rpm) | B: Time (min) | C: Volume (ml) | Yield % |
|---|---|---|---|---|
| 1 | 4 | 1 | 3 | 58.8 |
| 2 | 0 | 1 | 2 | 29.3 |
| 3 | 0 | 5 | 4 | 17.7 |
| 4 | 2 | 3 | 3 | 55.6 |
| 5 | 2 | 5 | 3 | 60.9 |
| 6 | 0 | 5 | 3 | 65.8 |
| 7 | 0 | 1 | 3 | 16.8 |
| 8 | 4 | 5 | 3 | 68.2 |
| 9 | 0 | 3 | 4 | 49.6 |
| 10 | 4 | 3 | 4 | 74.7 |
| 11 | 0 | 1 | 4 | 31.3 |
| 12 | 2 | 5 | 4 | 52 |
| 13 | 2 | 3 | 3 | 63.8 |
| 14 | 2 | 3 | 3 | 40.4 |
| 15 | 2 | 1 | 4 | 32.2 |
| 16 | 2 | 3 | 3 | 46.9 |
| 17 | 0 | 3 | 3 | 29.2 |
| 18 | 4 | 1 | 2 | 40.7 |
| 19 | 2 | 5 | 2 | 50.1 |
| 20 | 4 | 5 | 2 | 58.5 |
| 21 | 0 | 5 | 2 | 46.9 |
| 22 | 2 | 3 | 3 | 34.4 |
| 23 | 4 | 1 | 4 | 98.6 |
| 24 | 4 | 3 | 3 | 58.4 |
| 25 | 4 | 3 | 2 | 46.3 |
| 26 | 2 | 3 | 3 | 53.4 |
| 27 | 2 | 3 | 2 | 45.1 |
| 28 | 2 | 1 | 2 | 43.1 |
| 29 | 2 | 3 | 4 | 64.7 |
| 30 | 2 | 1 | 3 | 40.6 |
| 31 | 4 | 5 | 4 | 77.8 |
| 32 | 0 | 3 | 2 | 32.8 |

Optimal shaking speeds and lysis time were determined. Based on this data, an optimal shaking speed was determined at 2× or at 100 R.P.M. with a total lysis solution contact time of 5 minutes appearing optimal.

Example 7

The performance of membranes treated with a lysis buffering solution for 5 minutes was assessed. RNA assay was made to determine the amount of *Legionella pneumophila* in the lysate.

The performance of treated membrane with the optimized lysis buffer testing high concentrations of *Legionella pneumophila* (~$10^4$ CFU/assay) cells.

| Lysis Buffer | STM | | STM + NP40 + DMSO | |
|---|---|---|---|---|
| Membrane Treatment | − | + | − | + |
| RNA Log Copies | 7.36 | 7.78 | 7.44 | 7.65 |
| | 7.47 | 7.71 | 7.47 | 7.67 |
| | 7.50 | 7.61 | 7.45 | 7.69 |
| Mean | 7.44 | 7.70 | 7.45 | 7.67 |
| STD | 0.08 | 0.08 | 0.02 | 0.02 |

STM = lithium lauryl sulfate
NP40 = nonyl phenol (40 EtO)
DMSO = dimethyl sulfoxide
− = no main filter pretreatment
+ = with main filter pretreatment

Example 8

Selected main filter membrane and lysis buffer performance were assessed at different concentrations of the target, *Legionella pneumophila* cells. No treatment indicates a lack of pretreatment of the filter. STM treatment indicates that the filter was pretreated with the lysis buffering solution.

The repeatability performance of the selected membrane and lysis buffer testing different concentrations of *Legionella pneumophila* cells.

| | | STM | | STM + NP40 + DMSO | |
|---|---|---|---|---|---|
| GF2.7 | | Mean | STD | Mean | STD |
| $10^1$ | No treatment | 4.06 | 0.20 | 3.93 | 0.02 |
| | STM treatment | 4.32 | 0.13 | 4.33 | 0.19 |
| $10^4$ | No treatment | 6.71 | 0.02 | 6.70 | 0.02 |
| | STM treatment | 6.89 | 0.01 | 6.89 | 0.08 |

Example 9

The repeatability of a device integrating the selected membrane and lysis buffer tested 5 log levels of *Legionella pneumophila* cells.

| | RNA Log Copies | | Yield | | |
|---|---|---|---|---|---|
| CFU/L | Mean | STD | Mean | STD | RSD |
| 19 | 4.23 | 0.48 | 80.03% | 68.48% | 85.57% |
| 190 | 5.00 | 0.12 | 24.21% | 7.04% | 29.08% |
| 1900 | 5.87 | 0.03 | 22.03% | 1.48% | 6.72% |

-continued

| | RNA Log Copies | | Yield | | |
|---|---|---|---|---|---|
| CFU/L | Mean | STD | Mean | STD | RSD |
| 19000 | 6.90 | 0.12 | 20.50% | 6.11% | 29.81% |
| 190000 | 8.18 | 0.11 | 16.91% | 3.99% | 23.62% |

Example 10

Testing was undertaken to determine the effect of an additional filtering step, after the main filtering. After prefiltering and main filtering with lysing, the lysate was passed through a PES 0.22 µm filter to retain unlysed cells and pass lysate as filtrate.

| | Means of RNA log copies | STD of RNA log copies |
|---|---|---|
| Blank solution | Negative | / |
| Before filtration | 5.53 | |
| through PES 0.22 | 5.47 | 5.48 | 0.05 |
| Filter | 5.44 | |
| After filtration | 5.44 | |
| through PES 0.22 | 5.40 | 5.41 | 0.03 |
| Filter | 5.39 | |

In certain exemplary aspects of the invention, the processes herein described takes less than 15 minutes from the time in which the sample collection is taken to obtain a stabilized biomaterial sample ready for transport to downstream testing. In other exemplary embodiments, stable extracts from the biomaterials are provided that retain stability for up to 72 hours at temperatures up to about 43° C.

In one exemplary embodiment, the prefiltration and main filtration steps are dead end filtering steps. Further, in varying embodiments, pretreatment of the main filter medium via surfactants or other retention enhancement agents may be employed. Surfactants may be present in concentration ranges of about 0.5% to about 5%. Further, when chelating reagents are utilized to pretreat the main filter membrane, these may be present in concentration of about 0.1 mM to 100 mM. These chelating reagents may comprise for example EDTA and EGTA etc. In further exemplary embodiments, salts may be used to pretreat the main filtration membrane, and these may be present in an amount of about 1-8 mM solutions, and in those cases in which organic solvents may be utilized for pretreatment of the main filtration medium, these may be present in an amount of about 1-10%.

Further, in order to improve lysing, the samples may be incubated at temperatures of about 30° C. to 100° C. Also, electrical fields may be employed to help release the intracellular material. Shaking, inverting, or vibration via impellers and the like may be utilized again as an aid or aids in the lysing operations. Shaking speeds of from about 10-350 RPM may be employed in those instances in which shaking may be found useful to enhance the lysing operation and the lysing operation may generally proceed for anywhere from about between 1 minute to 3 hours.

While we have shown and described herein certain embodiments of the invention, it is intended that there will be covered as well any change or modifications therein which may be made without the departing from the spirit and scope of the invention as defined in the appended claims.

What is claimed:

1. A method of treating a liquid sample having non-target microbiological particles, inorganic particles, and microbiological target species therein, wherein said microbiological target species are cellular microbiological organisms, and wherein said microbiological target species comprise target materials enveloped therein, said method comprising:
   (a) passing said liquid sample through a prefilter medium to allow said microbiological target species to pass through as filtrate and to retain said non-target biological particles and said inorganic particles thereon;
   (b) contacting said filtrate of (a) with a main filtration medium adapted to retain said microbiological species thereon as retentate, wherein the retention enhancement agent comprises a member or members selected from the group consisting of surfactants, chelate reagents, salts and organic solvents; wherein the retention enhancement agent maintains the integrity of the microbiological target species therein during the contacting step of (b) and prevents the microbiological target species from irreversibly adhering to the main filtration medium;
   (c) lysing said retentate from step (b) on the main filtration medium to form a lysate containing said target materials; and
   (d) contacting said lysate with a post filtration medium to retain any unlysed material thereon while allowing passage of said lysate therethrough as filtrate.

2. The method as recited in claim 1 wherein said target materials are intracellular nucleic acids.

3. The method as recited in claim 2 wherein said cellular microbiological organisms are selected from the group consisting of bacteria, algae, fungi, and prokaryotes.

4. The method as recited in claim 3 wherein said bacteria is *Legionella pneumophila.*

5. The method as recited in claim 4 wherein said prefilter medium comprises a filter membrane having pore sizes between about 1 μm to about 100 μm.

6. The method as recited in claim 4 wherein said main filtration medium comprises a filter membrane having pore sizes between about 0.01 μm to about 3.0 μm.

7. The method as recited in claim 6 wherein said main filtration medium comprises a filter membrane having pore sizes of between about 0.7 μm to about 2.7 μm.

8. The method as recited in claim 1 wherein said post filtration medium comprises a filter membrane having pore sizes between about 0.22 μm to about 0.45 μm.

9. The method as recited in claim 1 wherein said liquid sample is cooling water.

10. The method as recited in claim 1 wherein said lysate contains DNA.

11. The method as recited in claim 1 wherein said lysate contains RNA.

12. The method as recited in claim 1 wherein said step (c) comprises contacting said retentate with a lysing buffer solution.

13. The method as recited in 12 wherein said step (c) further comprises vibrating said retentate.

14. The method as recited in claim 1 wherein said step (c) comprises subjecting said retentate to ultrasonic vibration to aid in lysing said retentate.

15. The method as recited in claim 1 wherein said prefilter medium comprises a first nylon membrane and a second nylon membrane wherein the first nylon membrane is in an upstream flow orientation and the second nylon membrane is in a downstream flow orientation compared to the first nylon membrane, said first nylon membrane having pore sizes larger than the pores sizes of said second nylon membrane.

16. The method as recited in claim 15 wherein said first nylon membrane has pore sizes of about 20 μm and said second nylon membrane has pore sizes of about 10-11 μm.

17. The method as recited in claim 1 wherein said main filtration medium comprises a fiberglass filter membrane.

18. The method as recited in claim 1 wherein said retention enhancement agent comprises a member or members selected from the group consisting of surfactants in a concentration of about 0.5% to about 5%, chelate reagents in a concentration of about 0.1 mM to about 100 mM, salts in a concentration of about 1 mM to about 8 mM, and organic solvents in a concentration of about 1% to about 10%.

* * * * *

UNITED STATES PATENT AND TRADEMARK OFFICE
CERTIFICATE OF CORRECTION

| | | |
|---|---|---|
| PATENT NO. | : 8,158,405 B2 | Page 1 of 1 |
| APPLICATION NO. | : 12/215768 | |
| DATED | : April 17, 2012 | |
| INVENTOR(S) | : Boyette et al. | |

It is certified that error appears in the above-identified patent and that said Letters Patent is hereby corrected as shown below:

In Column 12, Line 16, in Claim 13, delete "12" and insert -- claim 12 --, therefor.

Signed and Sealed this
Sixteenth Day of October, 2012

David J. Kappos
*Director of the United States Patent and Trademark Office*